US009491966B2

(12) United States Patent
Moses et al.

(10) Patent No.: US 9,491,966 B2
(45) Date of Patent: Nov. 15, 2016

(54) DIHYDROXYBENZOATE POLYMERS AND USES THEREOF

(75) Inventors: Arikha Moses, New York, NY (US); Satish Pulapura, Bridgewater, NJ (US); Qing Ge, Plainsboro, NJ (US); Sarita Nethula, Somerset, NJ (US); Archana Rajaram, Monmouth Junction, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 670 days.

(21) Appl. No.: 12/598,559

(22) PCT Filed: May 2, 2008

(86) PCT No.: PCT/US2008/062582
§ 371 (c)(1),
(2), (4) Date: Feb. 1, 2010

(87) PCT Pub. No.: WO2008/137807
PCT Pub. Date: Nov. 13, 2008

(65) Prior Publication Data
US 2010/0129417 A1 May 27, 2010

Related U.S. Application Data

(60) Provisional application No. 60/915,673, filed on May 2, 2007.

(51) Int. Cl.
| | |
|---|---|
| A61K 31/65 | (2006.01) |
| A61F 2/00 | (2006.01) |
| A61K 31/496 | (2006.01) |
| A61P 25/00 | (2006.01) |
| A61P 27/02 | (2006.01) |
| A61P 9/00 | (2006.01) |
| C08G 63/133 | (2006.01) |
| C08L 67/02 | (2006.01) |
| A23L 3/3481 | (2006.01) |
| A61K 31/765 | (2006.01) |
| A61K 45/06 | (2006.01) |

(52) U.S. Cl.
CPC ............ *A23L 3/3481* (2013.01); *A61K 31/765* (2013.01); *A61K 45/06* (2013.01)

(58) Field of Classification Search
CPC .. A23L 3/3481; A61K 31/765; A61K 45/06; A61K 2300/00
See application file for complete search history.

(56) References Cited

U.S. PATENT DOCUMENTS

| | | |
|---|---|---|
| 4,689,424 A | 8/1987 | Shalaby et al. |
| 4,927,914 A | 5/1990 | Rosenquist |
| 4,980,449 A | 12/1990 | Kohn et al. |
| 5,030,516 A | 7/1991 | Wehrmann et al. |
| 5,099,060 A | 3/1992 | Kohn et al. |
| 5,194,581 A | 3/1993 | Leong |
| 5,216,115 A | 6/1993 | Kohn et al. |
| 5,317,077 A | 5/1994 | Kohn et al. |
| 5,587,507 A | 12/1996 | Kohn et al. |
| 5,658,995 A | 8/1997 | Kohn et al. |
| 5,670,602 A | 9/1997 | Kohn et al. |
| 5,968,895 A | 10/1999 | Gefter et al. |
| 6,048,521 A | 4/2000 | Kohn et al. |
| 6,120,491 A * | 9/2000 | Kohn et al. ................... 604/502 |
| 6,180,608 B1 | 1/2001 | Gefter et al. |
| RE37,160 E | 5/2001 | Kohn et al. |
| 6,319,492 B1 | 11/2001 | Kohn et al. |
| RE37,795 E | 7/2002 | Kohn et al. |
| 6,475,477 B1 | 11/2002 | Kohn et al. |
| 6,602,497 B1 | 8/2003 | Kohn et al. |
| 6,689,350 B2 * | 2/2004 | Uhrich ........................ 424/78.17 |
| 6,852,308 B2 | 2/2005 | Kohn et al. |
| 7,056,493 B2 | 6/2006 | Kohn et al. |
| 7,326,425 B2 | 2/2008 | Kohn et al. |
| 7,521,061 B2 | 4/2009 | Kohn et al. |
| 7,585,929 B2 | 9/2009 | James et al. |
| 8,636,753 B2 | 1/2014 | Buevich et al. |
| 2002/0151668 A1 | 10/2002 | James et al. |
| 2005/0165203 A1 | 7/2005 | Kohn et al. |
| 2006/0173065 A1* | 8/2006 | Bezwada ...................... 514/419 |
| 2006/0188547 A1 | 8/2006 | Bezwada |
| 2008/0241212 A1 | 10/2008 | Moses et al. |

FOREIGN PATENT DOCUMENTS

| | | |
|---|---|---|
| EP | 0452595 B1 | 8/1995 |
| EP | 1400856 A2 | 3/2004 |
| GB | 636429 A | 4/1950 |

(Continued)

OTHER PUBLICATIONS

Australian Examination Report for Application No. 2008247455 dated Sep. 25, 2012.
Australian Examination Report for Application No. 2008247455 dated Sep. 24, 2013.
Canadian Office Action for Application No. 2,686,214 dated Jan. 7, 2014.
U.S. Appl. No. 60/908,960, filed Mar. 29, 2007.
U.S. Appl. No. 60/864,597, filed Nov. 6, 2006.
U.S. Appl. No. 60/733,988, filed Nov. 3, 2005.
Japanese Office Action for Application No. 2010-506705 dated Dec. 26, 2012.

(Continued)

Primary Examiner — Suzanne Ziska
Assistant Examiner — Thurman Wheeler
(74) Attorney, Agent, or Firm — Sorell, Lenna & Schmidt LLP; Leo G. Lenna, Esq.

(57) ABSTRACT

The present invention is directed to polyphenolic polymers formed from dihydroxybenzoic acid (DHB) derivatives or from resorcinol derivatives, monomers which form such polymers, blends of the polymers with drugs and/or additional polymers, as well as medical devices formed from, coated with, impregnated by or coverings made with any of the foregoing polymers (with or without drugs) or blends (with or without drugs).

16 Claims, 3 Drawing Sheets

(56) References Cited

FOREIGN PATENT DOCUMENTS

| | | | |
|---|---|---|---|
| JP | 44-013954 B | 6/1969 | |
| JP | 02-219819 A | 9/1990 | |
| JP | 03-014827 A | 1/1991 | |
| JP | 04031431 A | 2/1992 | |
| JP | 06-503369 T | 4/1994 | |
| JP | 07-185307 * | 7/1995 | ............ B01J 13/16 |
| JP | 07185307 A | 7/1995 | |
| JP | 2000239543 A | 9/2000 | |
| JP | 2003313278 A | 11/2003 | |
| JP | 2006312740 A | 11/2006 | |
| JP | 2007217578 A | 8/2007 | |
| WO | 9748782 A1 | 12/1997 | |
| WO | WO9924107 A1 | 5/1999 | |
| WO | 9952962 A1 | 10/1999 | |
| WO | 0107396 A1 | 2/2001 | |
| WO | WO0107396 A1 | 2/2001 | |
| WO | 0149249 A2 | 7/2001 | |
| WO | 0149311 A1 | 7/2001 | |
| WO | 03091337 A1 | 11/2003 | |
| WO | 2008121816 A2 | 10/2008 | |

OTHER PUBLICATIONS

Japanese Office Action for Application No. 2010-506705 dated Aug. 22, 2013.
International Search Report for Application No. PCT/US08/62582 dated Aug. 4, 2008.
Supplementary European Search Report and Search Opinion; European Patent Application No. 08747608.1; mailing date Feb. 27, 2015.

* cited by examiner

DIHYDROXYBENZOATE POLYMERS AND USES THEREOF

CROSS-REFERENCE TO RELATED APPLICATIONS

This Application is the National Stage of International Application No. PCT/US08/62582, filed May 2, 2008, and claims the benefit of U.S. Provisional Application No. 60/915,673, filed May 2, 2007; each of which is herein incorporated by reference in its entirety for all purposes.

The present invention is directed to polyphenolic polymers formed from dihydroxybenzoic acid (DHB) derivatives or from resorcinol derivatives, monomers which form such polymers, blends of the polymers with drugs and/or additional polymers, as well as medical devices formed from, coated with, impregnated by or coverings made with any of the foregoing polymers (with or without drugs) or blends (with or without drugs).

BACKGROUND OF THE INVENTION

Biodegradable and resorbable polymers play an ever increasing role in medicine, particularly because the bulk and molecular properties are amenable to manipulation to produce resorbable or partially resorbable medical products that alleviate morbidities associated with permanent implants. These polymers also generally enable pharmaceutical formulations to provide site-specific and sustained-release drug delivery. Biodegradable and resorbable polymers are also find use, for example, as coatings on medical devices, e.g., drug-eluting stents, catheters, surgical meshes and other devices, and can create another means for site-specific drug delivery. Further, these types of polymers can be formed into fully resorbable articles, with or without drugs, such as suture material, screws, device envelopes and coverings, medical grade pastes or putties, and other articles.

The myriad number of potential of medical applications requires biodegradable and resorbable polymers to have an equally diverse physical, chemical and biological properties. For biocompatibility purposes, the polymers must be suitable for use in animals and humans and thus lack toxicity under conditions of use. The degradation products of these polymers must also be non-toxic. Physically and chemically, the solubility, miscibility and release properties of the polymers need to accommodate varying drug elution and loading properties from different medical products. For example, anesthetic delivery may only be needed for several hours, the course of antibiotic delivery may be needed for 7-10 days, and the delivery of an immunogen may span several weeks or months. The requirements for timing of polymer degradation and resorption are also variable. In some applications, the polymer may need to remain at its site of action for at least a year to achieve complete healing and transfer of load. In other cases, such as with soft tissue, a much shorter duration (days, weeks or a few months) of polymer longevity may be desirable; whereas in other cases, if the polymer serves as a delivery vehicle, the actual time until the polymer resorbs may not be critical, so long as it resorbs within a reasonable, physiologically-relevant period.

The articles, coatings and formulations found in medical applications involving biodegradable and resorbable polymers are manufactured by many methods—using techniques as varied as spray-coating, molding, weaving, spinning, solvent casting, simple mixing and more—under a variety of conditions—high or low temperature, solvents, pressure, shear forces and more. Furthermore, if the particular application includes one or more drugs (including any biological molecules), these entities may be temperature sensitive, have limited solubility in the polymer or any solvents used during manufacture or have other incompatibilities with the manufacturing process for a given article, coating or formulation.

No matter the genesis, the diversity of product characteristics, whether of physical, chemical or biological origin, imposes a challenge to polymer selection and design on the polymer chemist.

Many classes of biodegradable and resorbable polymers are well known in the art. However, a surprising few are found in FDA approved medical products. No matter the reason that industry focuses its efforts on using very few polymers, some of those polymers retain inherent limitations, such as the polylactic acid and polyglycolic acid polymers which have been known to cause inflammatory reactions, or are not amenable to conditions of manufacture or medical use (lack thermostability or tensile strength). Consequently, a need exists to explore new classes of biocompatible, biodegradable and resorbable polymers for medical applications.

The present invention meets these needs by providing a new class of polymers based on dihydroxybenzoic acid (DHB) derivatives which are biodegradable and resorbable as well as on resorcinol derivatives. These biocompatible polymers allow the polymer chemist to select from an increasingly diverse array of polymers for medical applications.

SUMMARY OF THE INVENTION

The present invention is directed to new DHB- and resorcinol-derived biocompatible, biodegradable and/or resorbable polymers for use in a variety of medical applications. The DHB-derived polymers comprise one or more monomer units represented by the formula

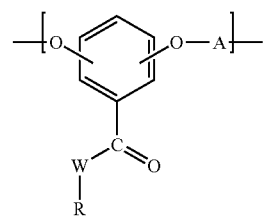

wherein

A is C(O), C(O)—$R_1$—C(O), C(=NH), C(O)—NH—$R_1$—NH—C(O) or C(S);

W is O, NH or S

R is hydrogen, an ester or amide protecting group, a leaving group, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, $(R_2)_rO((CR_3R_4)_aO)_s(R_2)_r$, a sugar, a pharmaceutically-active compound, or a biologically-active compound, wherein each a is independently 1-4, each b is independently 0 or 1, r is independently 1-4, and each s is independently 1-5000;

each $R_1$ is, independently, a divalent, linear or branched, substituted or unsubstituted alkyl, alkenyl, aryl, alkylaryl, alkylene oxide or arylene oxide moiety having from 1 to 30 carbon atoms, $(R_2)_rO((CR_3R_4)_aO)_s(R_2)_r$, or $(R_2)_rCO_2$ $((CR_3R_4)_aO)_sCO(R_2)_r$, where each a is independently 1 to 4, each r is independently 1 to 4 and s is 1 to 5000;

each $R_2$ is independently linear or branched lower alkyl; and each $R_3$ and $R_4$ is independently hydrogen, or linear or branched lower alkyl.

Preferred DHB-derived polymers are those in which W is O; A is $C(O)$—$R_1$—$C(O)$; R is hydrogen, a linear or branched, substituted or unsubstituted, alkyl, alkenyl, alkynyl, aryl, alkylaryl or alkoxyether group having from 1 to 30 carbon atoms, or $(R_2)_rO((CR_3R_4)_aO)_s(R_2)_r$; and each $R_1$ is, independently, a divalent, linear or branched, substituted or unsubstituted alkyl having from 1 to 30 carbon atoms, $(R_2)_rO((CR_3R_4)_aO)_S(R_2)_r$, or $(R_2)_rCO_2((CR_3R_4)_aO)_SCO(R_2)_r$.

The resorcinol-derived polymers comprise one or more monomer units represented by the formula

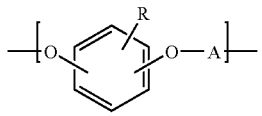

wherein

A is $C(O)$, $C(O)$—$R_1$—$C(O)$, $C(=NH)$, $C(O)$—NH—$R_1$—NH—$C(O)$ or $C(S)$;

R is hydrogen, halo, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, $(R_2)_bC(O)OR_2$, $(R_2)_rO((CR_3R_4)_aO)_s(R_2)_r$, a sugar, a pharmaceutically-active compound, or a biologically-active compound, wherein each a is independently 1-4, each b is independently 1 to 4, r is independently 1-4, and each s is independently 1-5000;

each $R_1$ is, independently, a divalent, linear or branched, substituted or unsubstituted alkyl, alkenyl, alkylene oxide or arylene oxide moiety having from 1 to 30 carbon atoms, $(R_2)_rO((CR_3R_4)_aO)_s(R_2)_r$, or $(R_2)_rCO_2((CR_3R_4)_aO)_sCO(R_2)_r$, where each a is independently 1 to 4, each r is independently 1 to 4 and s is 1 to 5000;

each $R_2$ is independently linear or branched lower alkyl; and each $R_3$ and $R_4$ is independently hydrogen, or linear or branched lower alkyl.

Preferred resorcinol-derived polymers are those in which A is $C(O)$—$R_1$—$C(O)$; R is hydrogen or a linear or branched, substituted or unsubstituted alkyl group having from 1 to 30 carbon atoms; and each $R_1$ is, independently, a divalent, linear or branched, substituted or unsubstituted alkyl having from 1 to 30 carbon atoms, $(R_2)_rO((CR_3R_4)_aO)_s(R_2)_r$, or $(R_2)_rCO_2((CR_3R_4)_aO)_sCO(R_2)_r$.

Another aspect of the invention is directed to compositions, including pharmaceutical compositions for controlled or sustained release, which comprise a polymer of the invention and one or more drugs. The compositions are suitable for any compatible drug, and include antimicrobial agents, anesthetics, anti-inflammatory agents, anti-scarring agents, anti-fibrotic agents, and chemotherapeutic agents. Compositions can be in the form of microspheres, nanospheres, gels, foams, scaffolds, coatings and the like.

A further aspect of the invention is directed to medical devices which are made from one or more of the polymers of the invention. Such devices can be fully or partially resorbable depending on the medical indication of the device. The devices can also be coated with a polymer of the invention. The medical devices made from the polymers or coated with the polymers can further comprise one or more drugs. Such devices are implanted, they enable, for example, drug elution in a site-specific manner. Such devices include stents, surgical meshes, pacemaker pouches, and more. A similar range of drugs as for compositions can be incorporated into the devices of the invention.

Yet another aspect of the invention relates to blends of polymers of the invention with one or more second polymers, such as blends of two polymers of the invention or blends of a polymer of the invention with a different class of polymers. Such blends can be used in the compositions and devices and further may include drugs in accordance with the invention.

A still further aspect of the invention is directed to a method of treating a disorder or condition in a patient comprising implanting the medical device of any of the foregoing claims in a patient, wherein said disorder is a cardiovascular disorder, a neurological disorder, a soft tissue defect, an ophthalmic condition, an anatomical repair, reconstruction, replacement or augmentation.

DETAILED DESCRIPTION OF THE INVENTION

Figure 1:
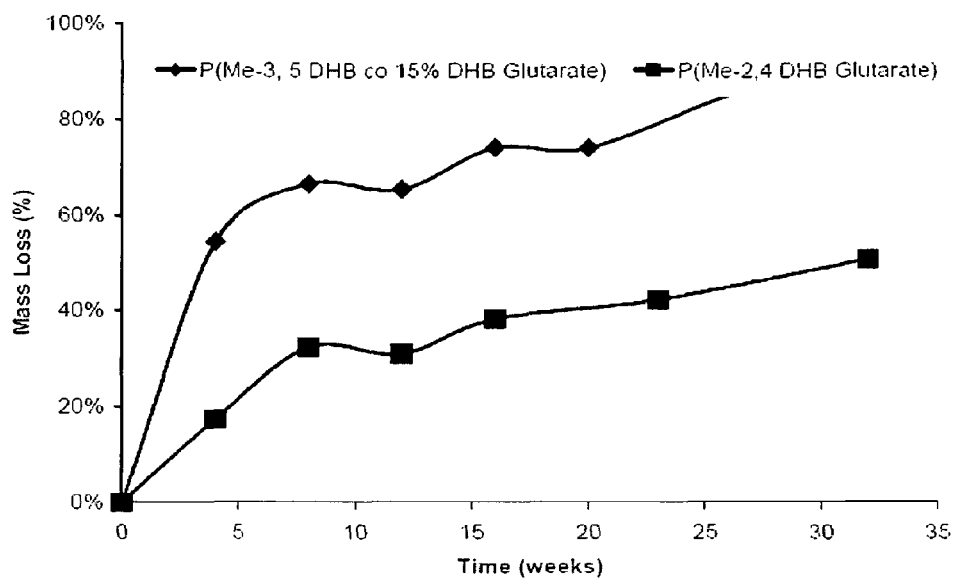
FIG. 1 graphically illustrates mass retained under physiological degradation conditions for MeDHB(3,5)-15% DHB glu and MeDHB(2,4) glu.

Definitions and Abbreviations:

The compounds herein described may have asymmetric centers. All chiral, diastereomeric, and racemic forms are included in the present invention. Geometric isomers of olefins and the like can also be present in the compounds described herein, and all such stable isomers are contemplated in the present invention.

By "stable compound" or "stable structure" is meant herein a compound or molecule that is sufficiently robust to survive isolation to a useful degree of purity from a reaction mixture, and for formulation into or use as an efficacious therapeutic agent.

As used herein, unless otherwise clear from the context, "alkyl" means both branched- and straight-chain, saturated aliphatic hydrocarbon groups having the specified number of carbon atoms. Straight and linear are used interchangeably. As used herein "lower alkyl" means an alkyl group having 1 to 6 carbon atoms. When substituted, the substituents can include halide, alkyl, alkoxy, hydroxy, amino, cyano, nitro, trifluoromethyl, trifluoroethyl, additional substituents as described herein, and the like compatible with the synthesis of the molecules of the invention.

As used herein, "alkenyl" means hydrocarbon chains of either a straight or branched configuration and one or more unsaturated carbon-carbon double bonds, such as ethenyl, propenyl, and the like. "Lower alkenyl" is an alkenyl group having 2 to 6 carbon atoms. As used herein, "alkynyl" means hydrocarbon chains of either a straight or branched configuration and one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl means having from 1-20 carbon atoms. Alkylene and alkenylene groups are alkyl groups and alkenyl groups, respectively, which are divalent. When substituted, the substituents can include halide, lower alkyl, alkoxy, hydroxy, amino, cyano, nitro, trifluoromethyl, trifluoroethyl, additional substituents as described herein, and the like compatible with the properties and synthesis of the molecules of the invention.

As used herein, "saturated or unsaturated alkyl" refers to any of an alkyl group an alkenyl group or an alkynyl group, having any degree of saturation, i.e., completely saturated (as in alkyl), one or more double bonds (as in alkenyl) or one or more triple bonds (as in alkynyl).

Examples of alkyl groups include but are not limited to, methyl, ethyl, n-propyl, isopropyl, n-butyl, isobutyl, t-butyl, pentyl, hexyl, n-heptyl, n-octyl, isooctyl, nonyl, decyl, and the like; alkylene and alkenylene groups include but are not limited to, methylene, ethylene, propylenes, propenylene, butylenes, butadiene, pentene, n-hexene, isohexene, n-heptene, n-octene, isooctene, nonene, decene, and the like. Those of ordinary skill in the art are familiar with numerous linear and branched hydrocarbon groups. Alkynyl groups include ethynyl and propynyl groups.

As used herein, "aryl" means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. When substituted, the substituents can include halide, alkyl, alkoxy, hydroxy, amino, cyano, nitro, trifluoromethyl, trifluoroethyl, additional substituents as described herein, and the like compatible with the properties and synthesis of the molecules of the invention.

As used herein, "alkylaryl" refers to moiety in which an aryl group is attached to an alkyl group, which in turn is the attachment point of the substituent. For example, a benzyl ester represents an alkylaryl moiety in which the methylene attached to a phenyl ring is bonded to the oxygen of the ester. The aryl group of this moiety can optionally be substituted in accordance with the definitions herein.

The term "substituted" as used herein means that one or more hydrogens on the designated atom are replaced with a selection from the indicated groups, provided that the designated atom's normal valency is not exceeded, and that the substitution results in a stable compound. If no substituent is indicated then the valency is filled with a hydrogen.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted.

A "halide" or a "halo" group is a halogen atom, and includes fluoro, chloro, bromo and iodo groups. The term "alkoxy" refers to an alkyl group having at least one oxygen substituent represented by R—O—.

Examples of poly(alkylene glycols) include, but are not limited to, poly(ethylene oxide)(PEG), poly(propylene glycol)(PPG), poly(tetramethylene glycol), and any derivatives, analogs, homologues, congeners, salts, copolymers and combinations thereof.

Abbreviations used herein for naming polymers and the subunits thereof include DHB, dihydroxybenzoic acid; Bz, benzyl; Et, ethyl; glu, glutarate; Me, methyl; PEG, polyethylene glycol; succ, succinate; Res, resorcinol; dig, diglycolate.

The nomenclature for the polymers has a first part that identifies the polyphenolic moiety (DHB or resorcinol derivatives) and a second part that identifies the A portion of the repeating unit.

If the first part of the monomer unit is an ester or amide, or a substituent, that group is generally listed first in the abbreviations. Hence, MeDHB is the ester form, namely dihydroxybenzoate methyl ester. When a free acid is present (rather than or in addition to an ester), there is no need for an initial group. Thus, DHB is the free acid form.

The second part of the name identifies the group with which the polyphenolic moiety is polymerized, such as the diacid, the carbonate, the iminocarbonate and the like. Hence, specific examples include poly(DHB glutarate), poly (DHB carbonate) and the like.

If a mixture of polyphenol moieties or of copolymerized groups (such as two diacids) are present in the polymer, then that part of the name may include the designation "co" or may have a hyphen, along with an indication of percentage of one of the two moieties. For example, poly(MeDHB: 10DHB-co-succinate) and poly(MeDHB-10-DT succinate) can be used interchangeably to mean a polymer made by copolymerizing a mixture of 90% dihydroxybenzoate methyl ester and 10% dihydroxybenzoic acid with the diacid succinic acid. An example of a mixed diacid is poly (MeDHB-co-50:50 PEG600-bis-glutarate glutarate).

As used herein, "therapeutically-effective amount" refers to that amount of a drug or bioactive agent necessary to administer to a host to achieve a desired therapeutic effect in treating, ameliorating or preventing a disease or condition. For example, a therapeutically-effective amount can be that amount to provide antimicrobial activity, pain relief, anti-inflammatory activity, antifibrotic activity, cell growth inhibition, or modulation of a cellular process associated with the particular drug or biological agent in use. Therapeutically-effective amounts for known drugs are available in the literature or can be determined, for new or known drugs, using methods, techniques and standards found in the literature.

Polymer Description & Synthesis

A biocompatible polymer is a polymer which is compatible with living tissue or a living system and is acceptable for use in or by animals or humans. Thus, a biocompatible polymer does not cause physiological harm to any significant or unacceptable degree. For example, biocompatibility can be assessed by showing that a biocompatible polymer does not cause any or any significant amount of inflammation or immunological reaction or is not toxic or injurious to the living tissue or system. Hence, a biocompatible polymer can be ingested, implanted, placed on or otherwise used in a living subject or tissue without untoward effects.

As used herein, a "biodegradable polymer" is a biocompatible polymer that is hydrolytically labile, oxidatively labile, or susceptible to enzymatic action, or any combination thereof, which action leads to the breakdown, whether partial or complete, of the polymer into components that are passively or actively removed from the implantation site by biological mechanisms. It should be understood that polymers which are biodegradable have variable resorption times, which can depend, for example, on the nature and size of the breakdown products as well as other factors.

As used herein a "resorbable polymer," is a biocompatible polymer which in its entirety or whose degradation products are capable of being taken up and/or assimilated in vivo or under physiological conditions by any mechanism (including by absorption, solubilization, capillary action, osmosis, chemical action, enzymatic action, cellular action, dissolution, erosion and the like or any combination of these processes) in a subject on a physiologically-relevant time scale consonant with the intended biological use of the polymer.

For resorbable polymers that contain cleavable backbone bonds, which when broken produce smaller water soluble fragments, those fragments may be polymeric or monomeric. These smaller fragments are or can be (as needed) further degraded to a size that can be engulfed by a macrophage, processed by a cell or otherwise removed from the cellular milieu or tissues at the physiological site of use, resulting in complete or substantially complete resorption of the polymer in a specified time.

When resorbable polymers become completely or substantially resorbed, then the polymer (but not necessarily the monomeric repeating units thereof or smaller polymeric fragments thereof) is no longer present or detectable in the subject. For example, if the polymer is a coating on an implanted medical device, the polymer would no longer be present on or detectable on the device. Of course, partial resorption may also be observed, especially if assessed in an early phase of the resorption process. Similarly, if the polymer is formed into a medical device (e.g., suture material, a staple, a device covering, an implant, a plug) or a sustained release composition (e.g., a drug formulation or vaccine carrier), then the device or composition is no longer present or detectable at the physiological site of administration. Without wishing to be bound, one can describe this process as conversion of a water-insoluble polymer into water soluble components or subunits by break down into its components with concomitant elimination or excretion of those components.

The time scale of resorption depends upon the intended use. The polymers of the invention can be manipulated to provide for rapid resorption, e.g., within a few days, to longer periods, such as weeks or months, under physiological conditions. Medically-relevant time periods include, e.g., from 1-30 days and from 1 to 24 months, as well as all time in between such as 5 days, 1-6 weeks, 2, 3, 4, 6 or months and the like.

In accordance with the invention, the subject polymers are DHB- or resorcinol derived biodegradable and/or resorbable polymers. For the DHB-derived polymers, the embodiments of the invention provide a biocompatible, biodegradable polymer comprising one or more monomer units represented by the formula

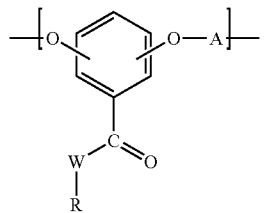

wherein
A is C(O), C(O)—$R_1$—C(O), C(=NH), C(O)—NH—$R_1$—NH—C(O) or C(S);
W is O, NH or S R is hydrogen, an ester or amide protecting group, a leaving group, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, $(R_2)_rO((CR_3R_4)_aO)_s(R_2)_r$, a sugar, a pharmaceutically-active compound, or a biologically-active compound, wherein each a is independently 1-4, each b is independently 0 or 1, r is independently 1-4, and each s is independently 1-5000;

each $R_1$ is, independently, a divalent, linear or branched, substituted or unsubstituted alkyl, alkenyl, aryl, alkylaryl, alkylene oxide or arylene oxide moiety having from 1 to 30 carbon atoms, $(R_2)_rO((CR_3R_4)_aO)_s(R_2)_r$, or $(R_2)_rCO_2((CR_3R_4)_aO)_sCO(R_2)_r$, where each a is independently 1 to 4, each r is independently 1 to 4 and s is 1 to 5000;

each $R_2$ is independently linear or branched lower alkyl; and each $R_3$ and $R_4$ is independently hydrogen, or linear or branched lower alkyl.

The OH groups can be at any two positions on the benzyl ring of the DHB. In some embodiments the hydroxyls are at the 2,4 positions and in others they are at the 3,5 positions.

In some embodiments, when W is NH for the DHB derivatives or for resorcinol derivatives, then W and R taken together (for DHB derivatives) or R alone (fro resorcinol derivatives) are selected from the group consisting of $C_1$-$C_{18}$ alkylamino, —NHCH$_2$CO$_2$R', —NH(CH$_2$)$_q$ OR', —NH(CH$_2$CH$_2$O)$_p$R', —NH(CH$_2$CH$_2$CH$_2$O)$_p$R',

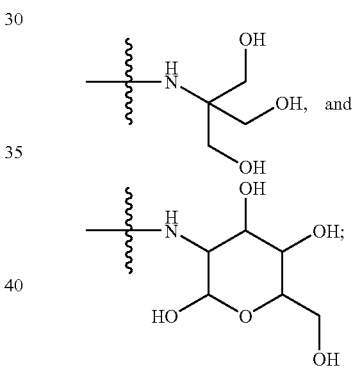

where q is 0 to 4, p is 1 to 5000, and R' is selected from the group consisting of H, $C_1$-$C_8$ alkyl, $C_2$-$C_8$ alkenyl, $C_8$-$C_{14}$ alkylaryl, benzyl, and substituted benzyl.

When R is an alkylene oxide, that group can be represented by the formula $(R_2)_rO((CR_3R_4)_aO)_s(R_2)_r$ (with a, r, s, $R_2$, $R_3$ and $R_4$ as defined above) which includes polyethylene glycol chains (PEG) such as —CH$_2$O(CH$_2$CH$_2$O)$_s$CH$_2$— or —CH$_2$CH$_2$O(CH$_2$CH$_2$O)$_s$CH$_2$CH$_2$— and polypropylene glycol chains such as —CH$_2$CH$_2$CH$_2$O(CH$_2$CH$_2$CH$_2$O)$_s$CH$_2$CH$_2$CH$_2$— and the like. Likewise, $R_1$ can be represented by the formula $(R_2)_rCO_2((CR_3R_4)_aO)_sCO(R_2)_r$. In a specific embodiment, this formula provides polymers which have PEG bis-succinate groups as A, namely A can be represented by the formula —C(O)CH$_2$CH$_2$C(O)O(CH$_2$CH$_2$O)$_s$C(O)CH$_2$CH$_2$C(O)—, where both $R_2$ s are ethylene and $R_3$ and $R_4$ together form an ethylene group. If the formula is the same except that both $R_2$ s are n-propylene, then the A moiety would be a PEG bis-glutarate.

R can also be a protected hydroxyl, protected amine or protected carboxylic group. In addition to the uses of the invention, in some instances, polymers having such protected substituents can be used as intermediates to prepare other polymers of the invention. Protecting groups for OH, $NH_2$ and COOH groups are well known in the art and any are suitable for use in accordance with the invention, provided they are stable and compatible with the synthetic methods used to produce the polymers of the invention.

In some embodiments, when R is aryl, and particularly a phenyl group forming a phenyl ester or a phenyl amide, that group can have from zero to five substituents present on the phenyl ring with each substituent independently selected from the group consisting of linear or branched, substituted or unsubstituted alkyl, aryl or alkylaryl having from 1 to 20 carbon atoms, a heteroatom-containing alkyl or aryl group, alkylcycloalkyl, alkoxy, alkyloxyamine, nitro, alkylether, —C(O)—$R_2$, —$(R_9)_b$C(O)—$YR_{10}$, X, a protected hydroxyl group, a protected amino group and a protected carboxylic acid group, where b is zero or one;

$R_2$ is linear or branched lower alkyl;

each $R_3$ and $R_4$ is independently hydrogen, or linear or branched lower alkyl; $R_9$ is lower alkylene or alkenylene;

$R_{10}$ is hydrogen, alkyl, aryl or alkylaryl having from 1 to 20 carbon atoms, or —$(R_2)_b$C(O)$OR_2$, or $(R_2)_rO((CR_3R_4)_aO)_s(R_2)_r$ with r being 1-4, a being 1-4 and s being 1-5000; and Y is O or NH.

Moreover, when R is a substituted phenyl group, the substituent can be (1) a substituted alkyl group, including those groups represented as —$CX_3$, —$CHX_2$, —$CH_2X$, —$R_2CX_3$, —$R_2CHX_2$ and —$R_2CH_2X$, wherein X is a halo group, and preferably are —$R_2CX_3$, —$R_2CHX_2$ and —$R_2CH_2X$, with $R_2$ as $CH_2CH_2$ and X as F or Cl;

(2) an alkylaryl group, including but not limited to a trityl group;

(3) an heteroatom-containing alkyl group including but not limited to trimethyl silane, glucosamine or N-hydroxysuccinimide;

(4) an heteroatom-containing aryl group;

(5) —$(R_9)_b$C(O)—$YR_{10}$, and $R_9$ is lower alkylene or alkenylene; $R_{10}$ is hydrogen, alkyl, aryl or alkylaryl having from 1 to 20 carbon atoms, or —$(R_2)_b$C(O)$OR_2$, or $(R_2)_rO((CR_3R_4)_aO)_s(R_2)_r$; and Y is O or NH, and preferably, when Y is O, b is zero, and $R_{10}$ is hydrogen, methyl, ethyl, propyl or benzyl, or alternatively, b is one, $R_9$ is methylene or ethylene, and $R_{10}$ is hydrogen, methyl, ethyl, propyl or benzyl;

(6) —$(R_9)_b$C(O)—$YR_{10}$, and $R_9$ is lower alkylene or alkenylene; $R_{10}$ is hydrogen, alkyl, aryl or alkylaryl having from 1 to 20 carbon atoms, or —$(R_2)_b$C(O)$OR_2$, or $(R_2)_rO((CR_3R_4)_aO)_s(R_2)_r$; and Y is O or NH, and preferably when Y is NH, b is zero, and $R_{10}$ is hydrogen, methyl, ethyl, propyl, benzyl or —$(R_{11})_b$C(O)$OR_2$, or alternatively, b is one, $R_9$ is methylene or ethylene, and $R_{10}$ is hydrogen, methyl, ethyl, propyl, benzyl or —$(R_{11})_b$C(O)$OR_2$, wherein $R_{11}$ is linear or branched lower alkylene, and further more when $R_{10}$ is —$(R_{11})_b$C(O)$OR_2$, $R_{11}$ is methylene or ethylene and $R_2$ is methyl or ethyl.

These substituted phenyls can have one R group, which can be at any position but is preferably at the 2 or 4 position on the aromatic ring. When two R groups are present, one is preferably at the 2 position and the other is at the 4 position on the aromatic ring.

The substituents of the invention include, as indicated, halo, hydroxy, alkyl, alkoxy, amino, cyano, nitro, trifluoromethyl, aryl, heteroaryl, monoalkylamino, dialkylamino and trialkylammonium and salts thereof and the others mentioned herein. These groups can be substituents for alkyl, alkenyl, cycloalkyl, aryl, alkylaryl, heteroaryl and heteroaralkyl groups as indicated in accordance with the invention. To create radioopaque polymers, one or more halide groups can be included at in possible position in the monomer or polymer. For example, a bromine or iodine can be a substituent on the DHB ring or can be a substituent on the ester, amide or thioester side chain.

$R_1$ is a divalent hydrocarbon group and can be linear or branched, substituted or unsubstituted. Such groups include alkyl, alkenyl, aryl, alkylaryl moieties having from 1 to 30 carbon atoms as well as larger alkylene oxide or arylene oxide moieties (based on the number of repeating units in those groups. As an example, when $R_1$ is an alkylene oxide, that group can be represented by the formula $(R_2)_rO((CR_3R_4)_aO)_s(R_2)_r$, (with a, r, s, $R_2$, $R_3$ and $R_4$ as defined above) which includes polyethylene glycol chains (PEG) such as —$CH_2O(CH_2CH_2O)_sCH_2$— or —$CH_2CH_2O(CH_2CH_2O)_sCH_2CH_2$— and polypropylene glycol chains such as —$CH_2CH_2CH_2O(CH_2CH_2CH_2O)_sCH_2CH_2CH_2$— and the like. Likewise, $R_1$ can be represented by the formula $(R_2)_rCO_2((CR_3R_4)_aO)_sCO(R_2)_r$. In a specific embodiment, this formula provides polymers which have PEG bis-succinate groups as A. for PEG bis-succinate, A is represented by the formula

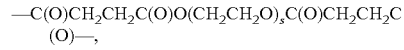
—C(O)$CH_2CH_2$C(O)O($CH_2CH_2$O)$_s$C(O)$CH_2CH_2$C(O)—, where both $R_2$ s are ethylene and $R_3$ and $R_4$ together form an ethylene group. If the formula is the same except that both $R_2$ s are n-propylene, then the A moiety would be a PEG bis-glutarate.

The preferred diacids formed by A include oxalic acid, malonic acid, succinic acid, glutaric acid, adipic acid, pimelic acid, suberic acid, azelaic acid, and sebacic acid, as well as diglycolic acid (where $R_1$ is —$CH_2OCH_2$—), dioxaoctanoic acid ($R_1$ is —$CH_2OCH_2CH_2OCH_2$—), alkylene oxide derivatives such as PEG, PEG bis-succinate and the like.

$R_2$, is independently a linear or branched lower alkylene or alkylenylene group. In preferred embodiments, $R_2$ is methylene, ethylene or propylene.

When present in the group $(R_2)_rO((CR_3R_4)_aO)_s(R_2)_r$, each $R_3$ and $R_4$ is independently a hydrogen or a linear or branched lower alkyl group. For example, if $R_3$ and $R_4$ are both hydrogen and a is 2, then that moiety is ethylene. Hence taken together and in combination with the value of a, $R_3$ and $R_4$ form a divalent alkyl groups, including but not limited to such as methylene, ethylene, propylene, butylene and the like.

The values of each a and each b are independently one of the whole numbers 1, 2, 3 or 4. The value of each r is independently one of the whole numbers 1, 2, 3 or 4.

The value of each s is independently about 1 to about 5000 and determines the number of repeat units in the alkylene oxide chain. Hence, s can range from 1 to about 10, to about 15, to about 20, to about 30, to about 40, to about 50, to about 75, to about 100, to about 200, to about 300, to about 500, to about 1000, to about 1500, to about 2000, to about 2500, to about 3000, to about 4000 and to about 5000. Additionally, when the length of the alkylene oxide chain is related as a molecular weight, such as with PEG 200, PEG 400, PEG 600 and the like, then s need not be a whole number but can also be expressed as a fractional value, representative of the average number of alkylene oxide repeating units based on the cited (or a measured) molecular weight.

When A is a carbonyl group, —C(O)—, then the polymers are polycarbonates. These polymers can be prepared by reaction with phosgene by methods known to those of skill in the art, including those described in U.S. Pat. No. 5,099,060.

When A is —C(O)—$R_1$—C(O)—, then A, taken with the oxygens in the backbone, forms a diacid (i.e., these diacid-based ester groups present in the backbone, when hydrolyzed, form a diacid). For simplicity, A is sometimes referred to herein as a diacid (though this is clearly not strictly in keeping with the actual definition of A as used in the claims but is clear in context).

When A is a diacid, the polymers are polyarylates. For these polyarylates (as well as other polymers of the invention), $R_1$ is a divalent hydrocarbon group and can be linear or branched, substituted or unsubstituted. Such groups include alkyl, alkenyl, aryl, alkylaryl moieties having from 1 to 30 carbon atoms as well as larger alkylene oxide or arylene oxide moieties (based on the number of repeating units in those groups. As an example, when $R_1$ is an alkylene oxide, that group can be represented by the formula $(R_2)_rO((CR_3R_4)_aO)_s(R_2)_r$, (with a, r, s, $R_2$, $R_3$ and $R_4$ as defined above) which includes polyethylene glycol chains (PEG) such as —$CH_2O(CH_2CH_2O)_sCH_2$— or —$CH_2CH_2O(CH_2CH_2O)_sCH_2CH_2$— and polypropylene glycol chains such as —$CH_2CH_2CH_2O(CH_2CH_2CH_2O)_sCH_2CH_2CH_2$— and the like. Likewise, $R_1$ can be represented by the formula $(R_2)_rCO_2((CR_3R_4)_aO)_sCO(R_2)_r$. In a specific embodiment, this formula provides polymers which have PEG bis-succinate groups as A. for PEG bis-succinate, A is represented by the formula

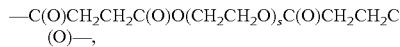

—C(O)CH$_2$CH$_2$C(O)O(CH$_2$CH$_2$O)$_s$C(O)CH$_2$CH$_2$C(O)—, where both $R_2$ s are ethylene and $R_3$ and $R_4$ together form an ethylene group. If the formula is the same except that both $R_2$ s are n-propylene, then the A moiety would be a PEG bis-glutarate.

The preferred diacids formed by A include oxalic acid, malonic acid, succinic acid, glutaric acid, adipic acid, pimelic acid, suberic acid, azelaic acid, and sebacic acid, as well as diglycolic acid (where $R_1$ is —$CH_2OCH_2$—), dioxaoctanoic acid ($R_1$ is —$CH_2OCH_2CH_2OCH_2$—), alkylene oxide derivatives such as PEG, PEG bis-succinate, PEG bis-glutarate and the like.

Methods of making polyarylates are known in the art. Such methods are found, for example, in U.S. Pat. Nos. 5,216,115; 5,317,077; 5,587,507; 5,670,602; 6,120,491; RE37,160E; and RE37,795E as well as in the literature, other patents and patent applications. Those of skill in the art can readily adapt these procedures to synthesize the polymers of the present invention.

When A is an imino group, —C(=NH)—, then the polymers are polyiminocarbonates. Polyiminocarbonates in general, and methods of their synthesis are described, e.g., in U.S. Pat. Nos. 4,980,449 and 5,099,060.

When A is —C(O)—NH—$R_1$—NH—C(O)—, then the polymers of the invention are polyurethanes. Polyurethanes can be prepared as known in the art, for example, by a condensation reaction between a diol and a diisocyanate of the formula O=C=N—$R_1$—N=C=O to produce polyurethanes of the invention. The $R_1$ group is as defined hereinabove.

When A is a thionyl group, —C(S)—, then the polymers of the invention are polythiocarbonates. These polymers can be prepared, for example, by reaction with thiophosgene by methods known to those of skill in the art.

Preferred DHB-derived polymers of the invention include are polyesters defined wherein W is O; A is C(O)—$R_1$—C(O); R is hydrogen, a linear or branched, substituted or unsubstituted, alkyl, alkenyl, alkynyl, aryl, alkylaryl or alkoxyether group having from 1 to 30 carbon atoms, or $(R_2)_rO((CR_3R_4)_aO)_s(R_2)_r$; and each $R_1$ is, independently, a divalent, linear or branched, substituted or unsubstituted alkyl having from 1 to 30 carbon atoms, $(R_2)_rO((CR_3R_4)_aO)_s(R_2)$, or $(R_2)_rCO_2((CR_3R_4)_aO)_sCO(R_2)_r$.

Preferred R groups for these polymers are hydrogen, methyl, ethyl, phenyl or benzyl. Preferred $R_1$ groups for these polymers have the A moiety being a diacid such that $R_1$, when taken with the two carbonyl groups of the diacid, forms succinate, glutarate, adipate, suberate, bis-carboxypolyethylene glycol, polyethyleneglycol-bis-succinate, polyethyleneglycol-bis-glutarate.

For the resorcinol-derived polymers, the embodiments of the invention provide a biocompatible, biodegradable polymer comprising one or more monomer units represented by the formula

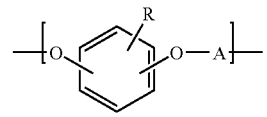

wherein
A is C(O), C(O)—$R_1$—C(O), C(=NH), C(O)—NH—$R_1$—NH—C(O) or C(S);

R is hydrogen, halo, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, $(R_2)_bC(O)OR_2$, $(R_2)_rO((CR_3R_4)_aO)_s(R_2)_r$, a sugar, a pharmaceutically-active compound, or a biologically-active compound, wherein each a is independently 1-4, each b is independently 1 to 4, r is independently 1-4, and each s is independently 1-5000;

each $R_1$ is, independently, a divalent, linear or branched, substituted or unsubstituted alkyl, alkenyl, alkylene oxide or arylene oxide moiety having from 1 to 30 carbon atoms, $(R_2)_rO((CR_3R_4)_aO)_s(R_2)_r$, or $(R_2)_rCO_2((CR_3R_4)_aO)_sCO(R_2)_r$, where each a is independently 1 to 4, each r is independently 1 to 4 and s is 1 to 5000;

each $R_2$ is independently linear or branched lower alkyl; and each $R_3$ and $R_4$ is independently hydrogen, or linear or branched lower alkyl.

Within the limits set forth above, each of R, $R_1$, $R_2$, $R_3$, $R_4$ and A are as defined hereinabove Preferred resorcinol derived polymers of the invention are those in which A is C(O)—$R_1$—C(O); R is hydrogen or a linear or branched, substituted or unsubstituted alkyl group having from 1 to 30 carbon atoms; and each $R_1$ is, independently, a divalent, linear or branched, substituted or unsubstituted alkyl having from 1 to 30 carbon atoms, $(R_2)_rO((CR_3R_4)_aO)_s(R_2)_r$, or $(R_2)_rCO_2((CR_3R_4)_aO)_sCO(R_2)_r$. The preferred R is hydrogen or methyl and the preferred $R_1$, when taken with the two carbonyl groups as a diacid, forms succinate, glutarate, adipate, suberate, bis-carboxypolyethylene glycol, polyethyleneglycol-bis-succinate, polyethyleneglycol-bis-glutarate. The preferred resorcinol derivatives are resorcinol (with the O moieties in the 1,3 positions) and hydroquinone (with the O moieties at the 1,4 positions).

The polymers of the invention can be homopolymers or copolymers. For example, a copolymer can be formed from a mixture of monomers with W as O and R as an alkyl group or as a benzyl group. The benzyl group can be selectively removed and converted to the free acid, which can be used as is or derivatized to create other polymers of the invention.

When the polymers are copolymers, they contain from at least about 0.01% to 100% of the repeating monomer units, from at least about 0.05, 0.1, 0.5, 1, 2, 3, 4, 5, 6, 8, 10, 12% to about 30, 40, 50, 60, 75, 90, 95 or 99% in any combination of ranges. In certain embodiments, the range of repeating units in free acid form in the polymer is from about 5 to about 50% (i.e., R is H—typically prepared via an intermediate in which R is benzyl), with the remaining R groups being alkyl or another R substituent. Additionally, the copolymers can have varying ratios of the A moiety when applicable, e.g., two different diacids or two different urethanes.

Examples of DHB-derived polymers of the invention having mixed R groups are those where the DHB monomer units in the polymer have R ranging overall from about 99% alkyl to about 50% alkyl with the remaining R being benzyl or hydrogen. Another example has R being about 95% to about 80% methyl and about 5% to about 80% benzyl or hydrogen.

Examples of DHB-derived polymers of the invention having A as a diacid and mixed $R_1$ groups such that $R_1$ ranges overall from about 10% to about 50% bis-carboxypolyethylene glycol with the remaining $R_1$ being alkylene or $R_1$ ranges overall from about 10% to about 50% polyethylene glycol-bis-succinate or polyethylene glycol-bis-glutarate with the remaining $R_1$ being alkylene. Preferred alkylene groups for these polymers form the diacids succinic acid, glutaric acid, adipic acid or suberic acid.

Hence those polymers of the invention which are copolymers containing a DHB- or resorcinol-derived monomer unit can have other monomer units that are nearly the same as the first monomer unit but with R being variable, e.g., hydrogen (to form a free COOH group), one or more different esters such as alkyl esters, alkylaryl esters, or esters with alkylene oxide chains or ether chains, by amides or by another compatible functional group. Alternatively, these slight variations can be combined with others where the DHB- or resorcinol-derived monomer unit may be the same but the variability resides among the different substituents, i.e., the changes are in any of A, $R_1$, $R_2$, $R_3$, and the other variable substituents.

Hence, in some embodiments, the DHB- or resorcinol-derived monomer unit can be substantially different and be a diphenol rather than a poly phenol. Examples of suitable diphenols are described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as in U.S. Patent Application Publication Nos. 2002/0151668; 2003/0138488; 2003/0216307; 2004/0254334; 2005/0165203; and in PCT Publication Nos. WO99/52962; WO 01/49249; WO 01/49311; WO03/091337 and in U.S. Ser. No. 60/733,988, filed Nov. 3, 2005.

A shorthand notation for the position of the hydroxyl is indicated as MeDHB(2,4) or as Me-2,4 DHB and both are equivalent names for 2,4-dihydroxybenzoate methyl ester. Similarly, the shorthand notations EtDHB(3,5) or Et-3,5 DHB are equivalent names for 3,5-dihydroxybenzoate ethyl ester, etc. Examples of polymers of the invention are shown below.

MeDHB(2,4)-Glu is poly(2,4-dihydroxybenzoate methyl ester glutarate);

MeDHB(2,4)-Sub is poly(2,4-dihydroxybenzoate methyl ester suberate);

MeDHB(3,5)-15% Peg600-Glu is poly((3,5-dihydroxybenzoate methyl ester)-co-(15% bis-carboxypolyethylene glycol 600:85% glutarate));

MeDHB(3,5)-5% Peg600-Glu is poly((3,5-dihydroxybenzoate methyl ester)-co-(5% bis-carboxypolyethylene glycol 600:95% glutarate));

MeDHB(3,5)-15% DHB-Glu is poly((85% 3,5-dihydroxybenzoate methyl ester:15% dihydroxybenzoic acid)-co-glutarate);

EtDHB(3,5)-Succ is poly(3,5-dihydroxybenzoate ethyl ester succinate);

EtDHB(3,5)-50% PegbisSucc-Adipate is poly(3,5-dihydroxybenzoate ethyl ester-co-(50% polyethylene glycol 400-bis-succinate:50% adipate));

MeDHB(3,5)-25% Peg8k bisSucc-Glu is poly(3,5-dihydroxybenzoate methyl ester-co-(25% polyethylene glycol 8000-bis-succinate:75% glutarate));

MeDHB(3,5)-25% Peg3350 bisSucc-Glu is poly(3,5-dihydroxybenzoate methyl ester-co-(25% polyethylene glycol 3350-bis-succinate:75% glutarate));

5-Me-resorcinol-glutarate is poly(5-methylresorcinol glutarate);

5-Me-resorcinol-15%-(3,5)-DHB-glutarate is poly((85% 5-methylresorcinol:15% 3-5-dihydroxybenzoic acid)-co-glutarate);

MeDHB(3,5)-10%-DHB(3,5)-suberate is poly((90% 3,5-dihydroxybenzoate methyl ester:10% dihydroxybenzoic acid)-co-suberate); and EtDHB(3,5)-glutarate is poly(3,5-dihydroxybenzoate ethyl ester glutarate).

Additional polymers of the invention include:

MeDHB(3,5)-10PEGacid-glu is poly(3,5-dihydroxybenzoate methyl ester)-co-(10% bis-carboxypolyethylene glycol 600:90% glutarate));

MeDHB(3,5)-50PEGglu3 is poly(3,5-dihydroxybenzoate methyl ester-co-(25% polyethylene glycol 3350-bis-succinate:75% glutarate)); and MeDHB(3,5)-10PEGglu3 is poly(3,5-dihydroxybenzoate methyl ester-co-(10% polyethylene glycol 600-bis-succinate:90% glutarate)).

Preferred polymers of the invention include MeDHB(3,5)-15% DHB-glu, MeDHB(3,5)-10PEGacid-glu, MeDHB(3,5)-50PEGglu3, and MeDHB(3,5)-10PEGglu3.

Some polymers of the invention and their characteristics are shown in Table 1. The MW column provides the molecular weight of the polymer as determined by gel-permeation chromatography; the Tg column provides the glass transition temperature (Tg) of the polymer as determined by differential scanning calorimetry (unless indicated by mp as a melting point or not determined, ND).

TABLE 1

| Polymer | Mw (kDa) | Tg (° C.) |
| --- | --- | --- |
| Me-3,5 DHB-5% Peg600 Acid-95% Glutarate | 44 | 36 |
| Me-3,5 DHB-10% Peg 600 Acid 90% Glutarate | 64 | 17 |
| Me-3,5 DHB-15% Peg 600 Acid 85% Glutarate | 45 | 8 |
| 85% Me-3,5 DHB-15% DHB Glutarate | 40 | 62 |
| 85% Me-3,5 DHB-15% DHB Succinate | 40 | 82 |
| Me-3,5 DHB-50% PEG400 bis Glu-50% Glutarate | 41 | −23 |
| Me-3,5 DHB-50% PEG400 bis Suc-50% Succinate | 90 | −8 |
| Me-3,5 DHB-10% PEG400 bis Glu-90% Glutarate | 70 | 11 |
| Me-3,5 DHB-15% PEG400 bis Glu-85% Glutarate | 76 | 6 |
| Me-3,5 DHB-20% PEG400 bis Suc-80% Succinate | 70 | 8.5 |
| Me-3,5 DHB-25% PEG3350 bis Suc-75% Glutarate | 94 | 48 (Mp) |

TABLE 1-continued

| Polymer | Mw (kDa) | Tg (° C.) |
|---|---|---|
| Me-3,5 DHB-25% PEG8000 bis Suc-75% Glutarate | 154 | 52 (Mp) |
| Et-3,5 DHB-50% PEG400 bis Suc-50% Adipate | 27.5 | −13.8 |
| Me-2,4 DHB Glutarate | 37 | 50 |
| Me-2,4 DHB Suberate | 59 | 19 |
| Et-3,5 DHB Succinate | 37 | 65 |
| Et-3,5 DHB Glutarate | 47 | 42 |
| Et-3,5-DHB diglycolate | 42 | 30 |
| Me-3,5 DHB Glutarate | 76 | 59 |
| 85% 5 Me-Res-15% 3,5 DHB Glutarate | 62 | 56 |
| 85% Me-3,5 DHB-15% 3,5 DHB Suberate | 41 | 24 |
| 85% Me-3,5 DHB-15% Benzyl 3,5-DHB glutarate | 53 | 44 |
| 85% Me-3,5 DHB-15% 3,5-DHB glutarate | 41 | 61 |
| Me-3,5 DHB co10%-Benzyl3,5 DHB suberate | 64 | ND |
| Me-3,5 DHB co10% 3,5 DHB suberate | 41 | 24 |
| N-Benzyl-3,5-DHB glutarate | 49 | 70 |
| 45% N-Benzyl-3,5 DHB-co-45% Me-3,5 DHB-co-10% Benzyl-3,5 DHB glutarate | 20 | 63 |
| N-Benzyl-3,5DHB-co-25% PEG600-diacid 75% glutarate | 76 | 25 |
| Resorcinol glutarate | 89 | 25 |
| 5-methyl-resorcinol glutarate | 92 | 41 |
| 5-methyl-resorcinol isopropylidene tartarate | 22 | 78 |
| 5-methyl-resorcinol-co-15% Benzyl-3,5 DHB glutarate | 68 | ND |
| 5-methyl-resorcinol-co-15% 3,5 DHB Glutarate | 62 | 52 |
| Hydroquinone-co-22.7% PEG600 Diacid 77.3% Glutarate | 75 | 151 |

Uses

The polymers of the invention are biocompatible, biodegradable polymers or biocompatible resorbable polymers comprising monomer units with a polyphenolic backbone and can be manipulated to vary degradation times. When the polymer is driven to breakdown more quickly into more water-soluble constituents, for example in polymers with free acid monomers, the result is faster resorption in use, especially when compared to a similar polymer where the free acids are replaced with alkyl esters.

Breakdown of the polymer can be measured in a variety of ways. The in vivo degradation process can be mimicked in vitro in several ways. By aging a polymer-coated device (or a composition or device formed primarily from a polymer of the invention) at 37° C. in phosphate buffered saline at pH 7.4, the hydrolytic processes may be reproduced. If oxidative mechanisms are relevant then the same solution may be supplemented with oxidants such as hydrogen peroxide or superoxide salts. Additionally, if enzymatic degradation processes are important, representative enzymes can be added to the solution. It is to be understood that while such in vitro tests can mimic the chemical processes operant in vivo, they predict kinetics and rates inaccurately. Further, as needed, in vivo animal models can be used to correlate in vivo and in vitro degradation behavior.

In addition to measuring polymer degradation and resorption, those of skill in the art can monitor drug release using the same techniques as well as others. For example, antibiotic activity can be measured by zone of inhibition assays, pain relief can be measured in animal models for pain and more.

The polymers of the invention are relatively more hydrophobic before breakdown, and this provides a useful ability to solublize drugs or act as a reservoir for a wide variety of drugs, in addition to being able to manipulate the drug release profile. Since a variety of substituents can be used on the polymers, such as PEGs, hydrophobic groups and many others, the polymer can be readily manipulated for purposes of both drug formulations and for controlled or sustained release. Those of skill in the art can thus manipulate the chemical constituents of the polymers to achieve particular release profiles for compositions, for coated devices or for resorbable devices (whether fully or partially resorbable)— in the context of the desired resorption times by the selecting particular polymers of the invention.

Hence, the polymers of the invention have a myriad of biological uses when a biocompatible, biodegradable and/or resorbable polymer is needed, for coating medical devices, to form fully or partially resorbable medical devices, to deliver drugs in specific manners (either in conjunction with such device or as part of a pharmaceutical composition comprising the polymer, a drug and other agents. It should be understood that the polymers are useful without the presence of drugs. For example, a polymer coating on a surgical mesh can increase mesh stiffness, and thereby allow easier handling at the time of implantation yet still provide a mesh that softens over time and is comfortable for the patient. Moreover, a polymer-coated, flat mesh can be formed into a three dimensional shape, and this can be useful in surgical repairs. Fully resorbable devices can be used as sutures intended to impart strength for a period before dissolving, as temporary wound closures, such as a femoral plug, and the like.

Further uses for the polymers of the invention are described in detail, for example, in U.S. Ser. No. 11/672,929, filed Feb. 8, 2007 which describes coated surgical meshes for a variety of applications; in U.S. Ser. No. 60/864,597, filed Nov. 6, 2006 which describes fully and partially resorbable coverings, pouches, bags and coated meshes for cardiac rhythm management devices, neurostimulators as well as for other implantable medical devices; and in U.S. Ser. No. 60/908,960, filed Mar. 29, 2007 and in PCT/US08/58652, filed Mar. 28, 2008 for resorbable coverings for breast implants.

The compositions of the present invention can be used to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and resorption rate; and (iv) that can be combined with drugs that are not only bioactive and/or biobeneficial but also control a physical property and/or a mechanical property of a medical article or coating formed from the polymer.

Blends:

An additional way to manipulate drug release and resorption characteristics is to blend polymers. Accordingly, the present invention provides blends of the polymers of the invention with other biocompatible polymers, preferably other biodegradable polymers. These other polymers include, but are not limited to, polylactic acid, polyglycolic acid and copolymers and mixtures thereof such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly (phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), o tyrosine-derived polyarylates, tyrosine-derived polycarbonates, o tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

Using blends provides many advantages, including the ability to make partially resorbable devices and fully resorbable devices that have varied resorption times for parts or all of the device. For example, a partially resorbable device may increase porosity over time and thus permit tissue in growth. Those of skill in the art can readily pick combinations of polymers to blend and determine the amounts of each polymer need in the blend to produce a particular product or achieve a particular result. For example, providing blends with a Tg in the range of about 20° to about 40° are particularly useful for medical applications.

Blends of the invention include, for example, formulations of MeDHB(3,5)-15% DHB-glu with each of MeDHB(3,5)-10PEGacid-glu, MeDHB(3,5)-50PEGglu3, and MeDHB(3,5)-10PEGglu3. Specific blends include Blend A (20% MeDHB(3,5)-15% DHB-glu and 80% MeDHB(3,5)-10PEGacid-glu) with a Tg of 33° C.; Blend B (60% MeDHB(3,5)-15% DHB-glu and 40% MeDHB(3,5)-50PEGglu3) with a Tg of 23° C.; and Blend C ((20% MeDHB(3,5)-15% DHB-glu and 80% MeDHB(3,5)-10PEGglu3) with a Tg of 29° C.

Drugs:

Any one or more drug, biological agent, or active ingredient that is compatible with the polymers, monomers and blends of the invention can be incorporated in, formed into or used in conjunction or combination with a pharmaceutical composition or a medical device coated or formed from the polymers, monomers or blends of the invention. Doses for such drugs and agents are known in the art. Hence, those of skill in the art can determine the amount of drug or agent desired for delivery, and calculate the amount needed for the desired application, based on size of the device, coating thickness, effective doses and the like.

In accordance with the invention, drugs and biologically-active agents include, but are not limited to, anesthetics, antimicrobials (which include antibiotics, antifungal agents and antibacterial agents), anti-inflammatory agents, fibrosis-inhibiting agents, anti-scarring agents, cell growth inhibitors, growth factors and the like.

As used herein, "drugs" is used to include all types of therapeutic agents, whether small molecules or large molecules such as proteins, nucleic acids and the like. The drugs of the invention can be used alone or in combination.

Examples of non-steroidal anti-inflammatory agents include, but are not limited to, acetominophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine.

Examples of anesthetics include, but are not limited to, lidocaine, bupivacaine, mepivacaine and xylocaine. Local anesthetics have weak antibacterial properties and can play a dual role in the prevention of acute pain and infection.

Examples of antimicrobial drugs include, but are not limited to, aminoglycosides such as amikacin, gentamicin, kanamycin, neomycin, streptomycin, and tobramycin;

antibiotics such as bacitracin, clindamycin, daptomycin, lincomycin, linezolid, metronid, polymyxin, rifaximin, vancomycin;

cephalosporins such as cephazolin;

macrolide antibiotics such as erythromycin, azithromycin and the like;

β-lactam antibiotics such as penicillins;

quinolones such as ciprofloxacin;

sulfonamides such as sulfadiazine;

tetracyclines such as minocycline and tetracycline; and other antibiotics such as rifampin, triclosan, chlorhexidine, sirolimus and everolimus.

Other drugs that can be used include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, nicotinic acid, chemodeoxycholic acid, chlorambucil and anti-neoplastic agents such as paclitaxel, sirolimus, 5-fluorouracil and the like. Examples of useful proteins include cell growth inhibitors such as epidermal growth factor antagonists. Likewise, growth stimulators, particularly for bone, such as BMP, bone morphogenic protein, can be included in compositions for use in inducing bone healing.

Preferred antimicrobial agents of the invention include rifampin, minocycline, gentamicin, vancomycin, triclosan, sirolimus and everolimus, alone or in combination. Rifampin and minocyline are a preferred combination of antimicrobial agents.

Leukotriene inhibitors/antagonists are anti-inflammatory agents and include, but are not limited to, leukotriene receptor antagonists such as acitazanolast, iralukast, montelukast, pranlukast, verlukast, zafirlukast, and zileuton.

Pharmaceutical Formulations:

The polymers and blends of the invention can be formulated as pharmaceutical compositions comprising one or more of those molecules, one or more drugs (as active ingredient), and a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are well known. In addition to the pharmacologically active agent, the compositions can contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds, as appropriate in oily injection suspensions may be administered. Suitable lipophilic solvents or vehicles include fatty oils, for example, sesame oil or synthetic fatty acid esters, for example, ethyl oleate or triglycerides. Aqueous injection suspensions can contain substances which increase the viscosity of the suspension include, for example, sodium carboxymethyl cellulose, sorbitol, and dextran. Optionally, the suspension can also contain stabilizers. Liposomes can also be used to encapsulate the agent for delivery into cells.

The pharmaceutical formulation for systemic administration according to the invention can be formulated for enteral, parenteral or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The polymers and blends of the invention can also be incorporated into pharmaceutical compositions which allow for the sustained delivery of those compounds to a mammal for a period of several days, to at least several weeks, to a month or more. Such formulations are described in U.S. Pat. Nos. 5,968,895 and 6,180,608 B1.

For topical administration, any common topical formation such as a solution, suspension, gel, ointment or salve and the like can be employed. Preparation of such topical formulations are well described in the art of pharmaceutical formulations as exemplified, for example, by Remington's Pharmaceutical Sciences. For topical application, the polymers and blends of the invention can also be administered as a powder or spray, particularly in aerosol form. The active ingredient can be administered in pharmaceutical compositions adapted for systemic administration. As is known, if a drug is to be administered systemically, it can be confected as a powder, pill, tablet or the like or as a syrup or elixir for oral administration. For intravenous, intraperitoneal or intralesional administration, the active ingredient can be prepared as a solution or suspension capable of being administered by injection. In certain cases, it may be useful to formulate the active ingredient in suppository form or as an extended release formulation for deposit under the skin or intramuscular injection. In a one embodiment, the polymers and blends of the invention may facilitate inhalation therapy. For inhalation therapy, the polymers or blends together, with the active ingredient, can be in a solution useful for administration by metered dose inhalers or in a form suitable for a dry powder inhaler.

Medical Devices:

The polymers and blends of the invention can be used to coat or form implantable prostheses used to reconstruct, reinforce, bridge, replace, repair, support, stabilize, position or strengthen any soft tissue defect. For example, soft tissue defects that can be treated in accordance with the instant invention include hernias, including but not limited to inguinal, femoral, umbilical, abdominal, incisional, intramuscular, diphragmatic, abdomino-throacic and thoracic hernias. The prosetheses can also be used for structural reinforcement for muscle flaps, to provide vascular integrity, for ligament repair/replacement and for organ support/positioning/repositioning such as done with a bladder sling, a breast lift, or an organ bag/wrap. The prosetheses can be used in recontruction procedures involving soft tissue such as an orthopaedic graft support/stabilization, as supports for reconstructive surgical grafts and as supports for bone fractures.

The prostheses are generally meshes, membranes or patches, and include woven or non-woven meshes and the like Additionally, the polymers and blends of the invention can be used to coat or to form wound closure adjuncts, such as staples, sutures, tacks, rings, screws, and the like.

The polymers and blends of the invention can also be used to coat meshes which are formed into or to form pouches, coverings, pockets and the like for implantable medical devices. Such implantable medical devices include, but are not limited to cardiac rhythm management devices such as a pacemaker, a defibrillator, a pulse generator as well as other implantable devices such as implantable access systems, neurostimulators, spinal cord stimulators, breast implants or any other implantable medical device. The coverings, pouches, pockets and the like hence can serve to secure those devices in position, provide pain relief, inhibit scarring or fibrosis, inhibit or prevent bacterial growth or infection, and deliver other drugs to the site of implantation.

The polymers and blends of the invention can also be used in conjunction with any implantable or insertable medical devices which has a temporary, or some time-limited therapeutic need as well as those with permanent function (such as joint replacements). For example, such polymers can be used to form fully resorbable vascular stents, which after a sufficient period of healing become completely resorbed while leaving a patent blood vessel. Fully resporbable stents may be used in conjunction with one or more drugs.

More detail and other examples of medical devices to which the present polymers and blends are useful include, but are not limited to, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, femoral plugs, patches, pacemakers and pacemaker leads, heart valves, vascular valves, biopsy devices, patches for delivery of therapeutic agent to intact skin and broken skin (including wounds); tissue engineering scaffolds for cartilage, bone, skin and other in vivo tissue regeneration; sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and various coated substrates that are implanted or inserted into the body.

Use of the polymers and blends with any of the medical devices described herein can include can be used with one or more drugs.

Accordingly, the present invention provides methods of treating a disorder or condition in a patient comprising implanting a medical device or a medical device assembly comprising a polymer or blend of the invention, e.g., as a coating, in conjuction with a covering or as the complete or partial device, by implanting the device in a patient, and particularly for disorders and conditions such as a cardiovascular disorder, a neurological disorder, a hernia or hernia-related disorder, an ophthalmic condition, or anatomical repair, reconstruction, replacement or augmentation.

In some embodiments, the method is used to implant a stent to treat atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

In other embodiments, the method is used to implant a surgical mesh to reconstruct, reinforce, bridge, replace, repair, support, stabilize, position or strengthen any soft tissue defect, including a hernia.

In yet other embodiments, the method is used to implant a medical device assembly such as a CRM in a covering or pouch, a neurostimulator in a pouch or covering, or a breast implant in a pouch or covering.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

EXAMPLES

Synthesis Procedure for Dihydroxy Benzoate Derivatives and Polymers of the Invention Dihydroxybenzoate derivative polymers and other polymers of the invention containing free acids can be prepared in a two-step process. In the first step, a precursor polymer containing a protected pendant group is prepared. In the next step, the pendant protecting group is removed without degrading the polymer backbone.

Step 1: Synthesis of Precursor Polymer

General Procedure

A dihydroxyphenol, diacid and DPTS are taken in a 3-neck flask equipped with an overhead stirrer and condenser. Methylene chloride is added to the flask and the contents stirred. After 15 min, when all the solids are well dispersed, DIPC is added and the mixture stirred until the reaction mixture is viscous. The polymer can be isolated by repeated precipitations from methylene chloride and isopropanol (IPA) (or other convenient solvent). Finally, the polymer solid is typically dried in a hood overnight, then transferred to a vacuum oven and dried to constant weight for one day.

Specific Procedure:

p(Me3,5-DHB-15%3,5-BnDHB-Glutarate)

3,5-DHB methyl ester (0.1487 mol, 25 g), 3,5-DHB benzyl ester (0.0266 mol, 6.5 g), glutaric acid (0.1753 mol, 23.2 g), dimethyaminopyridinium-para-toluenesulfonate (DPTS) (0.0584 mol, 17.2 g) were taken in a 500 ml 3neck flask equipped with an overhead stirrer and condenser. Methylene chloride (220 ml) was added to the flask and the contents are stirred. After 15 min, when all the solids were well dispersed diisopropylcarbodiimide (DIPC) (0.526 mol, 66.36 g, 82.13 ml) was added. The mixture was stirred for 20-22 h by which time reaction mixture was viscous. The polymer was isolated by repeated precipitations from methylene chloride and IPA. Finally the polymer solid was transferred to a polypropylene tray and left to dry in the hood overnight. It was then transferred to a vacuum oven at 40° C. and dried to constant weight for one day. Yield: 44.6 g (92%). MW=43 KDa. Tg=44° C.

Step 2: Removal of Protecting Group

General Procedure:

The benzyl polymer is dissolved in DMF and nitrogen is bubbled through the solution. After 15 min nitrogen flow is stopped and catalyst is added. Hydrogen gas is passed through the reaction mixture which is stirred overnight (until there is no benzyl). The polymer is isolated by precipitation into cold water and dried to constant weight under vacuum.

Specific Procedure p(Me3,5-DHB-15%3,5-DHB-Glutarate)

884 ml of DMF was used to dissolve the p(Me3,5-DHB-15Bn3,5-DHB-Glutarate)_polymer (44.2 g) and produce a 5% solution. The nitrogen was bubbled through the clear solution for about 30 minutes. The catalyst (5% Pd on BaSO4) 15.5 g (35% w/w with respect to the benzyl precursor polymer) was added in one shot. The hydrogen was bubbled and the stirring was continued overnight. The reaction mixture was filtered on celite bed. The polymer was isolated by precipitation into cold water. After filtration, the wet cake of the polymer was dried to constant weight under vacuum. Yield: 32.8 g. (74%). Mw: 41 KDa; Tg: 61° C.

Synthesis of Protected Monomer 3,5-dihydroxybenzoic acid (17.7 g, 0.115 mole), sodium bicarbonate (11.6 g, 0.138 mole) and benzyl bromide (20.5 ml, 0.173 mole) were stirred in dimethylformamide<40° C. for 7 h and diluted with 500 ml ethyl acetate. The suspension was extracted with water (400 ml) and 3% sodium bicarbonate/14% NaCl (2×400 ml) and 20% NaCl (2×200 ml). After drying over anhydrous magnesium sulfate the clear solution was concentrated to a white solid which was mixed in 150 ml of hexane and isolated by filtration. After vacuum drying, 17 g of product was collected: silica gel TLC (90:10:1): (methylene chloride:methanol: acetic acid) shows a single spot at Rf=0.39 with uv and iodine visualization, DSC: mp=132.9° C., purity=99.0%, NMR: 5.3 ppm(s, 2H), 6.5 ppm(s, 1H), 6.9 ppm (s, 2H), 7.4 ppm(m, 5H), 9.6 ppm (s, 2H).

The protected monomer can be derivatized and then used in polymerization reactions using methods known in the art.

Degradation Study Protocol

Molecular weight (MW) profile: For monitoring MW decrease as a function of time, polymer films are incubated with 0.01 M PBS or 0.01M PBS with Tween20 (50 to 100 mL) at 37° C. without shaking. At each time point, polymer samples are dissolved solvent, filtered and transferred to analysis vials for analysis by gel permeation chromatography (GPC).

Mass loss profile: For mass loss analysis, films are incubated with 0.01 M PBS or 0.01M PBS with Tween20 (50 to 100 mL) at 37° C. The buffer in the vials is changed at periodic intervals and analyzed for soluble degrading components. At each time point, 1-2 mL buffer from three small vials are filtered and transferred to analysis vials for analysis by reversed phase HPLC. Alternately, the devices can be washed, dried and weighed (final weight) and the mass loss determined by subtracting the final weight from the original weight.

Figure 2:
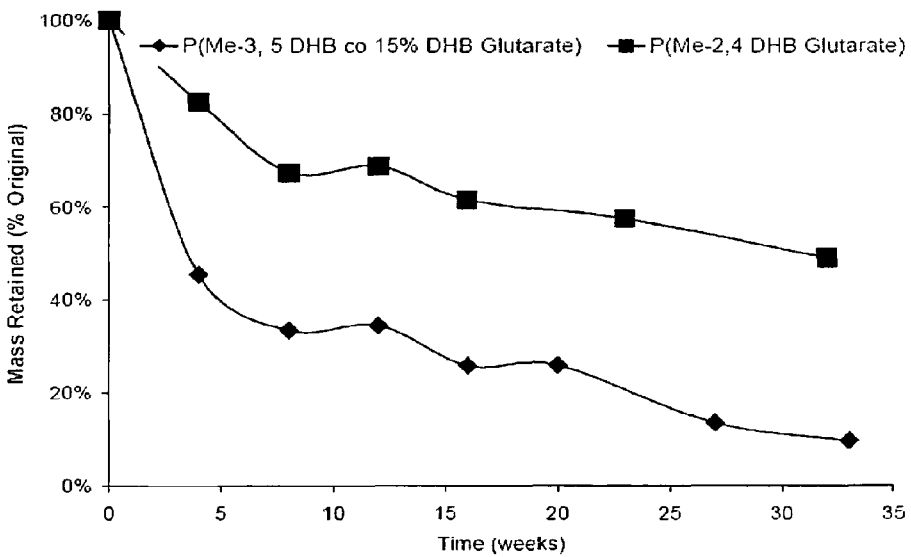
FIG. 2 graphically illustrates mass loss under physiological degradation conditions for MeDHB(3,5)-15% DHB glu and MeDHB(2,4) glu.
Figure 3:
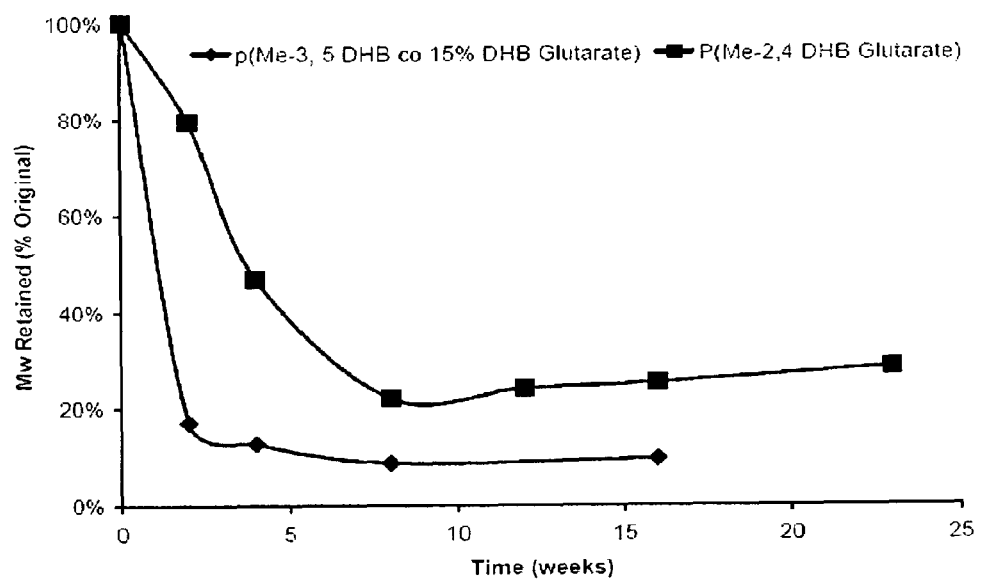
FIG. 3 graphically illustrates molecular weight retained under physiological degradation conditions for MeDHB(3,5)-15% DHB glu and MeDHB(2,4) glu.

The results for two DHB polymers are shown in FIGS. 1-3.

Drug Release from Polymer Blends

Figure 4:
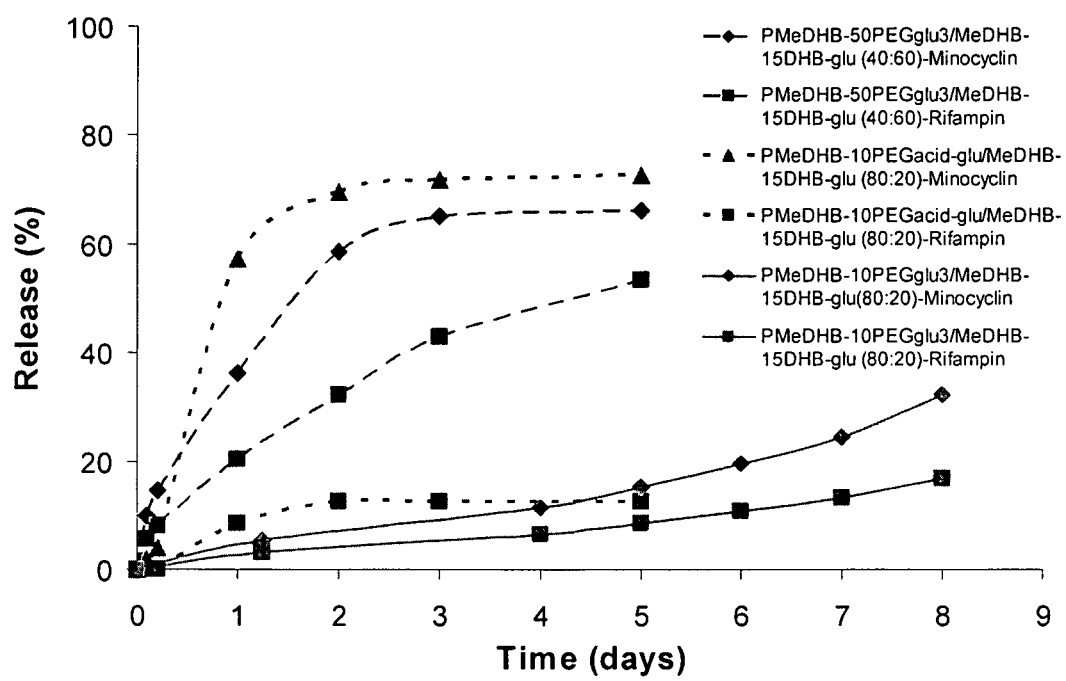
FIG. 4 shows the release profiles of minocycline and rifampin from three different polymer blends.

Blends A, B and C were prepared as generally described in U.S. Ser. No. 12/058,060, filed Mar. 28, 2008. Briefly, films of polymer blends were prepared for drug release studies by the indicated amounts of polymers, rifampin or minocyclin in solvent, casting films, and drying the films. The dried film was cut into small pieces and placed into a vial containing PBS. Aliquots of buffer were removed periodically for analysis and replaced with fresh buffer. Samples were analyzed by HPLC to determine the cumulative amount of released rifampin and minocycline (FIG. 4)

We claim:
1. A biocompatible, biodegradable polymer comprising one or more monomer units represented by the formula

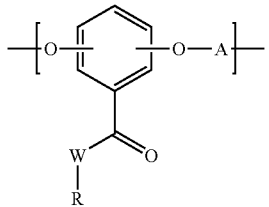

wherein A is C(=NH) or C(S); W is O, NH or S; R is hydrogen, an ester or amide protecting group, a leaving group, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, $(R_2)_rO((CR_3R_4)_aO)_s(R_2)_r$, a sugar, a pharmaceutically-active compound, or a biologically active compound, wherein each a is independently 1-4, r is independently 1-4, and each s is independently 1-5000; where each a is independently 1 to 4, each r is independently 1 to 4 and s is 1 to 5000; each $R_2$ is independently linear or branched lower alkyl; and each $R_3$ and $R_4$ is independently hydrogen, or linear or branched lower alkyl.

2. The polymer of claim 1, wherein W is O; and R is hydrogen, a linear or branched, substituted or unsubstituted, alkyl, alkenyl, alkynyl, aryl, alkylaryl or alkoxyether group having from 1 to 30 carbon atoms, or $(R_2)_rO((CR_3R_4)_aO)_s(R_2)$.

3. The polymer of claim 2, wherein R is hydrogen, methyl, ethyl, phenyl or benzyl.

4. The polymer of claim 2, wherein R is alkyl in about 50% to about 99% of the monomer units of the polymer, and R in the remaining monomer units is benzyl.

5. The polymer of claim 2, wherein R is alkyl in about 50% to about 99% of the monomer units of the polymer, and R in the remaining monomer units is hydrogen.

6. The polymer of claim 4 wherein R is methyl in about 80% to about 95% of the monomer units, and R is benzyl in about 5% to about 80% of the monomer units.

7. The polymer of claim 5 wherein R is methyl in about 80% to about 95% of the monomer units, and R is hydrogen in about 5% to about 80% of the monomer units.

8. A biocompatible, biodegradable polymer comprising one or more monomer units represented by the formula

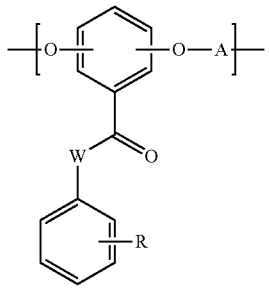

wherein A is C(=NH); W is O, NH or S; R is linear or branched, substituted or unsubstituted alkyl, aryl or alkylaryl having from 1 to 20 carbon atoms, a heteroatom-containing alkyl or aryl group, alkylcycloalkyl, alkoxy, alkyloxyamine, nitro, alkylether, —C(O)—$R_2$, —$(R_9)_bC(O)$—$YR_{10}$, X, a protected hydroxyl group, a protected amino group and a protected carboxylic acid group, where b is zero or one; $R_2$ is linear or branched lower alkyl; $R_3$ and $R_4$ is independently hydrogen, or linear or branched lower alkyl; $R_9$ is lower alkylene or alkenylene; $R_{10}$ is hydrogen, alkyl, aryl or alkylaryl having from 1 to 20 carbon atoms, or —$(R_2)_bC(O)OR_2$, or $(R_2)_rO((CR_3R_4)_aO)_s(R_2)_r$ where r is 1-4, a is 1-4 and s is 1-5000; X is F or Cl; and Y is O or NH.

9. The polymer of claim 8, wherein W is O.

10. The polymer of claim 9, wherein R is —C(O)—$R_2$.

11. The polymer of claim 10, wherein $R_2$ is methyl or ethyl.

12. The polymer of claim 8, wherein R is —C(O)—$R_2$, and $R_2$ is methyl or ethyl.

13. A biocompatible, biodegradable polymer comprising one or more monomer units represented by the formula

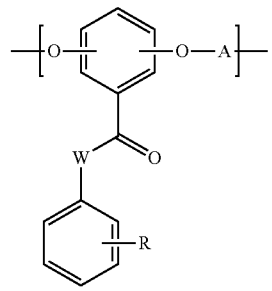

wherein A is C(=NH) or C(S); W is O, NH or S; R is linear or branched, substituted or unsubstituted alkyl, aryl or alkylaryi having from 1 to 20 carbon atoms, a heteroatom-containing alkyl or aryl group, alkylcycloalkyl, alkoxy, alkyloxyamine, nitro, alkylether, —C(O)—$R_2$, —$(R_9)_bC(O)$—$YR_{10}$, X, a protected hydroxyl group, a protected amino group and a protected carboxylic acid group, where b is zero or one; $R_2$ is linear or branched lower alkyl; $R_9$ is lower alkylene or alkenylene; $R_{10}$ is hydrogen, alkyl, aryl or alkylaryl having from 1 to 20 carbon atoms, or —$(R_2)_bC(O)OR_2$, or $(R_2)_rO((CR_3R_4)_aO)_s(R_2)_r$ where r is 1-4, a is 1-4 and s is 1-5000; X is F or Cl; and Y is O or NH.

14. The polymer of claim 13, wherein R is —C(O)—$R_2$.

15. The polymer of claim 14, wherein $R_2$ is methyl.

16. The polymer of claim 14, wherein $R_2$ is ethyl.

* * * * *